United States Patent [19]

Jones et al.

[11] Patent Number: 4,786,471

[45] Date of Patent: Nov. 22, 1988

[54] HETEROGENEOUS IMMUNOASSAY METHOD AND ASSEMBLY

[75] Inventors: Linda L. Jones, Los Angeles; Edward T. Maggio, San Diego, both of Calif.

[73] Assignee: Baxter Travenol Laboratories, Inc., Deerfield, Ill.

[21] Appl. No.: 544,177

[22] Filed: Oct. 21, 1983

[51] Int. Cl.[4] .......................... B65D 69/00; B01L 3/00
[52] U.S. Cl. ...................................... 422/61; 422/100; 422/102
[58] Field of Search .................................. 422/57–61, 422/102, 100; 436/536–542, 800, 804, 807, 808, 824; 435/7

[56] References Cited

U.S. PATENT DOCUMENTS

| 3,706,305 | 12/1972 | Berger et al. | 422/102 |
|---|---|---|---|
| 4,301,139 | 11/1981 | Feingers et al. | 422/61 |
| 4,357,240 | 11/1982 | Mehra et al. | 422/102 |
| 4,424,279 | 1/1984 | Bohn et al. | 422/61 |
| 4,458,020 | 7/1984 | Bohn et al. | 422/61 |

FOREIGN PATENT DOCUMENTS

| 2028822 | 12/1971 | Fed. Rep. of Germany | 422/102 |
|---|---|---|---|
| 66759 | 6/1981 | Japan | 422/61 |

Primary Examiner—Christine M. Nucker
Attorney, Agent, or Firm—R. A. Williams; P. C. Flattery; M. D. Hunter

[57] ABSTRACT

A method and assembly provided for the detection and determination of at least one ligand in a sample suspected of containing the ligand. The method includes providing in a hand-held assembly having a first chamber and a second chamber separated by a separation means which permits the passage therethrough of materials of a relatively small size while preventing the passage therethrough of materials of a relatively larger size; a suspension in the first chamber of an admixture of a binding partner for the ligand and a labeled component. The labeled component is selected from the group consisting of binding partner, compound which can bind to the binding partner, compound which can bind to the reaction product of the ligand and binding partner, and compound which can bind to the ligand. The sample suspected of containing the ligand is introduced to the first chamber. The mixture is incubated for a time sufficient to form a reaction mixture containing free labeled component and a complex of the labeled component, binding partner and ligand. The free labeled component is separated from the complex by creating a pressure differential across the separation medium whereby the relatively larger size complex remains in the first chamber while the relatively smaller size free labeled component passes to the second chamber. The presence of either the labeled component present in the complex in the first chamber or the free labeled component in the second chamber is determined. The determination of such labeled component in either chamber provides a measure of the presence and quantity of the ligand in the sample.

23 Claims, 1 Drawing Sheet

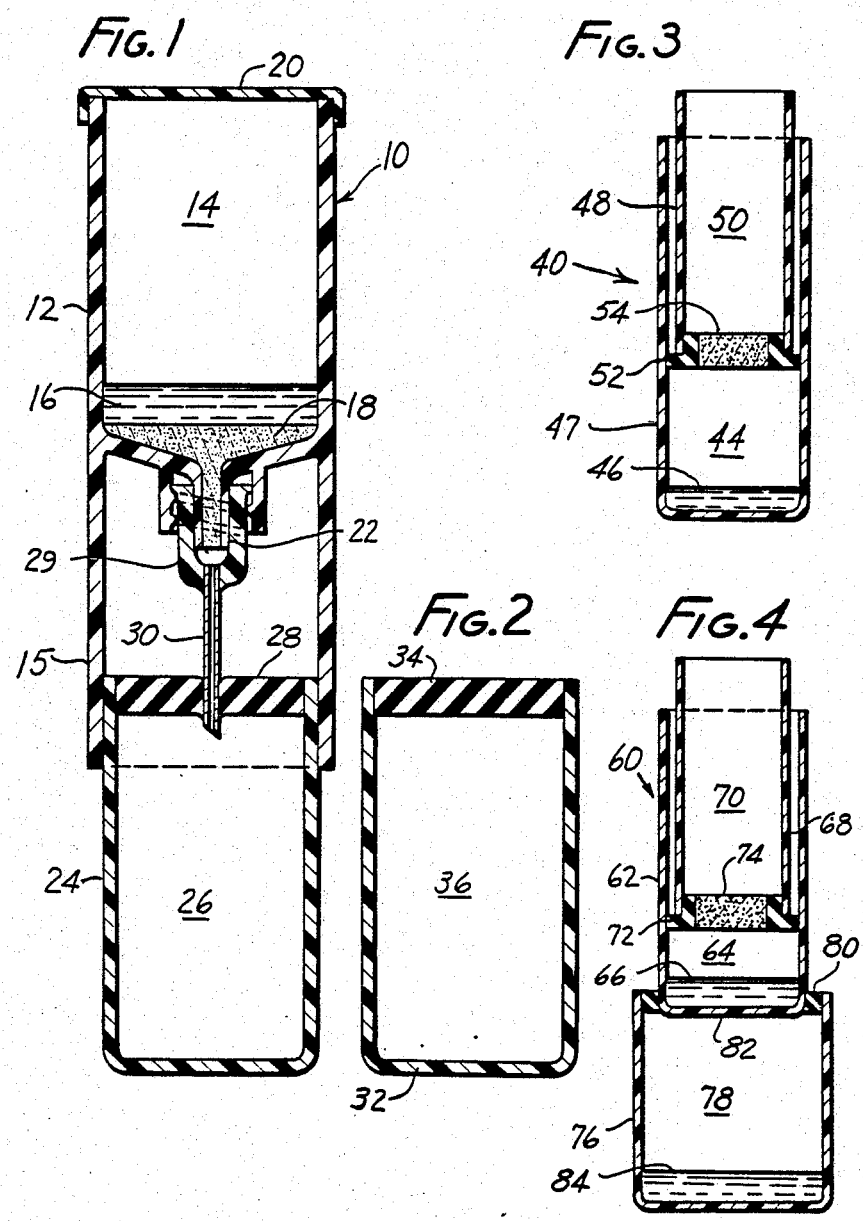

HETEROGENEOUS IMMUNOASSAY METHOD AND ASSEMBLY

BACKGROUND OF THE INVENTION

The invention herein relates to a simplified and safe diagnostic method and assembly for the rapid determination of ligands or antiligands which does not require special skills to perform.

There are a number of immunological methods which have been developed for the determination of a wide variety of ligands and antiligands. Generally such methods rely upon the interaction between an antigen and its antibody. Such methods provide a label to one of the components of the antigen antibody pair such that when the labeled component is introduced to a sample containing the unknown corresponding antigen or antibody for the labeled component, a reaction occurs which can be monitored by use of the label.

Antibodies or receptors have been utilized for many years in a wide variety of procedures for detecting or measuring antigens or ligands. In many of such techniques, results can be determined by simply measuring the signal produced from the antibody-antigen reaction. For example, some techniques provide an agglutination or precipitation upon reaction forming the antibody-antigen complex. However, many antibody-antigen reactions doe not readily produce measurable signals and it is often necessary to label one or the other component of the reaction and monitor the signal produced by that label.

Labeling of one of the components can be accomplished using various techniques. In the 1960's and 1970's, a commonly used label for the components consisted of the use of radioactive isotope. More recently, nonisotope labels such an enzyme, chemiluminescent, and fluorescent labels have been found to be more convenient and safe. Such labels have, therefore, gained in popularity.

Even with the advent of nonisotopic techniques, performance of immunoassays still requires highly skilled persons and relatively sophisticated laboratory equipment. With the changing economic environment, there is a need for safe, accurate, rapid, and relatively inexpensive immunoassay systems which are sufficiently simplified for nonlaboratory persons to perform in environments such as a doctor's office, a patient's bedside, satellite laboratory, or home environments. Unlike currently available laboratory procedures, methods intended for use by less skilled persons must also be designed to minimize the risk of spreading infectious disease agents potentially present in test samples.

Immunological methods can be categorized as competitive or noncompetitive binding assays and as heterogeneous or homogeneous assays. In competitive binding assays, an unknown ligand or antiligand and a similar predetermined component compete for binding sites on a binding partner. Either the binding partner or the competing component is labeled and the unknown is indirectly measured by determining the extent to which the labeled component is bound to the limited amount of binding partner. In noncompetitive binding assays, there is no added component that competes for the unknown's binding partner. The unknown is directly measured by determining the degree to which a labeled binding partner is bound directly or indirectly to the unknown.

The distinction between heterogeneous and homogeneous assays is based on whether a bound/free separation step is required. Homogeneous assays do not require physical separation of bound and free labeled components because results are based on the modulation of the label's signal when the labeled component is bound to its binding partner. Although the performance of homogeneous assays is relatively simple, they are less sensitive than heterogeneous assays and usually are limited to the measurement of smaller antigens. In addition, homogeneous assays require relatively expensive instrumentation to monitor the modulation of the label's signal.

Heterogeneous assays require physical separation to isolate bound labeled complex from free labeled component before results can be determined. Separation is generally accomplished by one of several methods including electrophoresis, filtration, adsorption, precipitation, and/or centrifugation. Because the separation step is a critical step in the procedure, performance has required either sophisticated, automated equipment or considerable care and precision on the part of a well trained technician.

An important consideration in working with heterogeneous assays is the potential for spread of infectious disease agents which can be present in the specimen being tested. At some time in the separation step, either a portion of the reaction mixture must be transferred to another vessel or free components are washed off a solid phase material. When such transfer or washing steps are performed manually, there is a considerable risk in contaminating surrounding areas or persons performing the procedures.

It would be desirable to provide an immunoassay with the broad application of heterogeneous assays which is also simple, rapid, accurate, and safe for unskilled persons to perform in environments outside of sophisticated laboratory settings, when single sample determinations are desired. Such an assay should be convenient and inexpensive, eliminate the need for critical washing steps, and reduce the risk of spreading infectious disease agents.

SUMMARY OF THE INVENTION

The invention herein is directed to a simplified heterogeneous competitive or noncompetitive immunoassay which utilizes filtration techniques in a self-contained, manually operable device which simplifies the assay procedure and reduces the risk of contamination. Separation is based upon molecular exclusion and the formation of antibody-antigen complexes that are significantly larger than the free labeled component. The filtration device provides the means to rapidly separate bound and free components in one easy step. In contrast with other commonly used separation systems, the filtration device utilized herein requires no special laboratory equipment, allows for the determination of bound and free components, and collects liquid test materials in self-contained receptacles.

The method and apparatus for the detection and determination of a ligand or ligands in a sample suspected of containing such ligand or ligands provide a simple, rapid, accurate and safe assay determination.

The method is practiced by providing in a liquid medium a suspension of a binding partner for the ligand or ligands to be determined. The suspension includes a labeled component which can be labeled by any suitable labeling techniques. The labeled component is a compound selected from the group consisting of binding partner, a compound which can bind to the binding partner, a compound which can bind to the reaction product of ligand and binding partner, and a compound which can bind to the ligand. The suspension is provided in a reaction chamber of a reaction vessel. The assembly herein also includes a separation medium which can be present in the reaction vessel, which can be introduced to the reaction vessel. The separation medium permits the passage therethrough of materials of a relatively small size while preventing the passage therethrough of materials of a relatively larger size. More particularly, the separation medium permits the passage of free labeled component while preventing the passage of the complex of labeled component, binding partner and ligand.

The sample suspected of containing the ligand is introduced to the reaction chamber. The resultant reaction mixture is incubated for a time sufficient to form a reaction mixture containing free labeled component and a complex of the labeled component, binding partner and ligand. Following the incubation, the resulting complex is separated from the free labeled component by creating a pressure differential across the separation means whereby the relatively larger size complex does not pass through the separation means. That is, the complex remains in the reaction chamber while the relatively smaller size free labeled component passes through the separation medium to a collection chamber.

The presence and quantity of the ligand in the sample can be determined by either determining the presence of the labeled component present in the complex remaining in the reaction chamber or by determining the presence of the free labeled component present in the collection chamber. Determining either the labeled component present in the complex or the free labeled component provides a measure of the presence and quantity of the ligand in the sample.

The filtration process can be completed by using either an evacuated tube as a source of negative pressure or a device requiring moderate manual positive pressure. Creating the pressure differential across the filter medium results in a clean, fast, and efficient separation of bound and free components which avoids messy transfer steps and multiple washing steps and their associated sources of error, as well as potential contamination and spread of diseases. Additionally, use of hand operated devices eliminates the requirement for special pumps or central vacuum lines, making it possible to perform rapid and accurate single sample determinations in field settings.

BRIEF DESCRIPTION OF THE DRAWINGS

The invention herein will be better understood with regard to the following detailed description and the accompanying drawings wherein:

FIG. 1 is a lateral cross-sectional view of a preferred assembly for practicing the invention herein;

FIG. 2 is a lateral cross-sectional view of a component of a kit for the practice of the method herein;

FIG. 3 is a lateral cross-sectional view of another embodiment of an assembly for practicing the method herein; and FIG. 4 is a lateral cross-sectional view of still another embodiment of an assembly for practicing the method herein.

DETAILED DESCRIPTION OF THE INVENTION

The invention herein is directed to a self-contained, manually operated assembly which is used for heterogeneous competitive or noncompetitive immunoassays and an improved method for performing heterogeneous competitive and noncompetitive immunoassays which utilizes filtration techniques in such a self-contained, manually operated assembly.

In the description of the invention herein, the following terms will have the following meanings:

ligand shall mean any compound for which a binding partner naturally exists or can be prepared;

binding partner shall mean any compound or composition capable of recognizing a particular spatial and polar organization of a molecule; and the term antibody is employed herein as illustrative of and more generally denote binding partner.

The assembly herein for performing the immunoassay method will be described with regard to the accompanying drawings. With regard to FIGS. 1 and 2, a preferred embodiment of an assembly for performing the immunoassay is illustrated. In FIG. 1, the assembly 10 includes a reaction vessel 12 defining a reaction chamber 14. Provided in the reaction chamber is a liquid medium containing a suspension 16 of a binding partner for the ligand to be determined or binding partners for the ligands to be determined in a sample. Although the term liquid medium is used, the binding partner can be initially provided in a solid state which will provide a suspension upon introduction of the sample to be evaluated, which sample can contain other liquid agents such as solvent, dispersants, anti-foam agents, buffers and the like. In some instances, the binding partner and labeled component are provided in a solid phase, such as a lyophilized state, to increase their stability and shelf life. They can be reconstituted by adding a liquid medium either before or during the performance of the assay herein. At the time of reaction between the ligand and binding partner, the components are preferably in a liquid medium. The term suspension is used herein in a generic sense and is meant to include suspensions, emulsions, dispersions and solutions.

Provided in the suspension 16 is a labeled component which can be labeled with any labeling technique which will provide a detectable label such as spectrophotometric labeling, radioisotope labeling, enzyme labeling, and the like. The suspension can also contain a macromolecular compound that is capable of binding to the ligand to be determined, the binding partner for such ligand or the complex formed by the coupling of the binding partner to the ligand. By providing such a macromolecular compound to the suspension, there is provided an enhancement of the relative size differential between the complex formed by the coupling of the ligand and binding partner and the free labeled component. The macromolecular compound can be selected from any compound which will provide substantial size differential between the free labeled component and the complex so as to enhance separation. Acceptable macromolecular compounds include agarose, gel beads, polyacrylimide beads and the like. A particularly preferred macromolecular compound is an agarose gel bead, commercially available as Sepharose 4B from Pharmacia.

The upper end of the reaction vessel 12 can be open to provide for introduction of the suspension to the chamber 14. It is preferred that the upper end of the reaction vessel be provided with a cap or top 20. Such a cap or top 20 can be fitted over the opening to the chamber to provide a seal and thereby inhibit the likelihood of spreading of infection from the sample which is introduced to the chamber. The top 20 can be removable to permit the introduction of a sample to be tested or the top 20 can be of a self-sealing material such that it can be punctured using a needle cannula for introducing the sample to be assayed and resealed upon withdrawal of the needle cannula.

The reaction vessel 12 is provided with an outlet 22 from which fluid can be withdrawn from the reaction vessel. As shown in FIG. 1, the outlet 22 can be fitted with a needle hub 29 having a needle cannula 30 attached thereto. The needle cannula can be provided with a cannula protector (not shown) to prevent inadvertent punctures. Cannula protectors are commercially available. In the embodiment shown in FIG. 1, inadvertent punctures are avoided by providing a downwardly extending wall portion 15 which aligns with the sidewall of the reaction vessel 12 and extends beyond the tip of the needle cannula. The downwardly extending wall portion can be flared at its lowermost end.

The assembly herein includes the provision of a collection chamber such as shown in FIG. 1 by providing a collection vessel 24 which includes a second chamber or collection chamber 26 therein. The collection vessel is provided with a puncturable top 28 which can be perforated by the needle cannula 30 attached to the reaction vessel 12. Providing a cover to the collection vessel prevents and/or inhibits the spreading of infection. The collection vessel has an outside diameter smaller than the inside diameter of the downwardly extending wall portion 15 of the reaction vessel.

The collection vessel can be provided with a port (not shown) for evacuating the vessel or the collection vessel can have a reduced pressure provided in the collection chamber therein. A reduced pressure in the collection chamber 26 can also be provided by puncturing the top 28 with a second needle cannula (not shown) which can be connected to a vacuum source. A reduced pressure provides upon puncturing of the top 28 by the needle cannula of the first reaction vessel a pressure differential across the separation medium 18. The reduced pressure causes fluid to flow through the separation medium and the resulting filtrate is collected in the collection chamber 26 of the collection vessel.

A pressure differential across the separation medium can be created by creating a greater pressure above the separation medium in the reaction chamber 14 than is provided in the collection chamber of the collection vessel. For example, a syringe-type plunger can be inserted into the reaction chamber and forces downwardly therethrough to create such a greater pressure.

The assembly herein can also include a second collection vessel 32 having a collection chamber 36 and a perforable top 34. The second collection vessel has an outside diameter less than the inside diameter of the downwardly extending wall portion 15. As in the first collection vessel 24, the second collection vessel 32 can have a previously formed reduced pressure in the collection chamber 36 or the ability to have a reduced pressure created in the chamber. The second collection vessel provides a vessel for monitoring and determining the presence of ligand in a sample being evaluated. That is, the second vessel provides a means for detecting the presence of the labeled component and thereby determining the presence of ligand. The function of the second collection vessel will be hereinafter more fully described.

The assembly shown in FIG. 1 is easy to use, avoids the likelihood of spreading of infectious agents which may be in a sample being tested, and can readily be used by one having little training. In use, the reaction vessel 12 contains a suspension 16 which includes a binding partner for the ligand to be determined and a labeled component. The labeled component is a compound having a detectable label and which is selected from the group consisting of a binding partner, a compound which can bind to the binding partner, a compound which can bind to the reaction product of the ligand and binding partner, and a compound which can bind to the ligand. The labeled component can be labeled using any convenient technique for binding the label to the particular component on which it is to be present in the suspension. That is, a label such an enzyme can be directly bound to a binding partner, such as an antibody, or it can be bonded to another compound which compound provides the binding capability to link the label to the component. The labeled component can also include a plurality of detectable labels on one particular compound. For example, the labeled component can be an enzyme labeled antibody wherein a plurality of enzymes are bound to one antibody. By providing such a plurality of detectable labels (enzymes) to the antibody, there is a corresponding increase in the sensitivity of the overall assay. That is, there would be a greater likelihood of detecting the presence of ligand as the ability to detect the label is increased by the enzyme substrate reaction due to the presence of such a plurality of enzyme labels.

The sample suspected of containing the ligand is introduced to the suspension in the reaction vessel. The sample can be introduced using a syringe and perforating the top of the reaction vessel with the needle cannula of the syringe. The reaction components are permitted to react for an incubation period which is determined by the particular ligand and binding partner reaction. During such time, the ligand, if available, complexes with the binding partner and the labeled component, leaving a reaction mixture containing the complex, which is labeled due to coupled with the labeled component, and free labeled component.

Separation of the complex from the free labeled component is performed by puncturing the top on the collection vessel 24 with the needle cannula 30. The collection vessel having a reduced pressure in the collection chamber creates a pressure differential across the separation medium causing fluid free labeled component and materials of a size sufficiently small to flow through the separation medium to flow through the separation medium to be collected as a filtrate in the collection chamber. The separation medium is selected such that the complex formed does not flow through the separation medium. Thus, the complex remains in the chamber 14 of the reaction vessel.

The presence of the ligand can be determined by either monitoring the presence of free labeled component collected in the filtrate in the collection chamber 26 or by monitoring the presence of the labeled component present in the complex in the reaction chamber 14. The method for detecting the presence of the label can be any suitable technique depending upon the label technique chosen. Determining the presence of the labeled component in the complex in the reaction chamber 14 is a direct measurement of the presence of the ligand. However, the label determining reaction in the reaction chamber 14 can be hampered by the presence of the complex. For example, if the label is an enzyme, and an enzymic color forming reaction is used to detect the presence of the enzyme, the color can be clouded by the presence of the complex. In order to provide a clear solution, the second collection vessel 32 can be used, which when punctured with the needle cannula 30 creates a pressure differential across the separation medium, causing the fluid to flow therethrough, leaving the complex remaining above the separation medium in the reaction chamber 14. The collected filtrate can then be observed to determine the occurrence of the label determining reaction.

The collection vessel 24 can be provided with label detecting reagents. By providing label detecting reagents in the collection vessel, the presence of free labeled component in the filtrate can be detected upon collection of the filtrate (i.e., upon separation).

A second assembly for performing the determination method herein is described with regard to FIG. 3. In FIG. 3, the assembly 40 includes a reaction vessel 42 containing a reaction chamber 44 and a suspension 46. The suspension 46 is as described with regard to the embodiment shown in FIG. 1.

The assembly also includes an inner collection vessel 48 which can be fitted within the reaction vessel 42. The inner collection vessel 48 contains a collection chamber 50. The annulus between the inner collection vessel and the reaction vessel is provided with a seal 52 which prevents fluid flow from the reaction chamber into the annulus between the vessels. A separation medium 54 is provided at the lower end of the inner collection vessel, which separation medium is as described with regard to the embodiment shown in FIG. 1. The inner collection vessel can be provided with a vented top.

The assembly shown in FIG. 3 is used by introducing a sample suspected of containing the ligand to the reaction chamber 44 and allowing the sample to mix with the suspension 46. The sample can be introduced after first separating the inner collection vessel from the reaction vessel. Following the addition of the sample, the inner collection vessel is slid into the reaction vessel to seal the reaction chamber. The reaction is permitted to occur for an incubation period wherein ligand present in the sample reacts with the binding partner and labeled component to form a complex of the ligand, binding partner and labeled component.

After the incubation period has passed, the inner collection vessel is pushed further into the reaction vessel and reaction chamber. As the inner collection vessel moves downwardly, it encounters the reaction mixture. The liquid in the reaction mixture and free labeled component flows through the separation medium 54, leaving remaining in the reaction chamber the formed reaction complex. When macromolecular molecules are used in the method to enhance separation, the macromolecular structure of the formed complex and free macromolecules (if any) remain. The presence of ligand can be determined by determining the presence of the free labeled component in the collection chamber 50 or by determining the presence of labeled component present in the complex in the reaction chamber 44. When the labeled component present in the complex is to be determined, the inner collection vessel can be removed, thereby enabling introduction of the labeled determining reagents directly to the complex present in the reaction chamber of the reaction vessel.

Another embodiment of the assembly herein is illustrated in FIG. 4. The assembly in FIG. 4 is similar to that in FIG. 3. With regard to FIG. 4, an assembly 60 includes a first reaction vessel 62 containing a reaction chamber 64. A suspension 66 is provided in the reaction chamber. The suspension is as described with regard to the embodiments shown in FIGS. 1 and 3.

Removably positioned within the reaction vessel 62 is a first collection vessel 68. The first collection vessel includes first collection chamber 70 and is provided with a seal 72 which prevents the flow of fluid from the reaction chamber into the annulus between the first collection vessel and reaction vessel. A separation medium 74 is provided at the lower end of the first collection vessel, which separation medium is as described with regard to the embodiments shown in FIGS. 1 and 3. The first collection vessel and reaction vessel have relative sizes which permits the sliding of the first collection vessel within the reaction chamber of the reaction vessel.

A second collection vessel 76 is attached to the lower end of the reaction vessel 62. A seal or gasket 80 can be provided to seal the annulus between the second collection vessel and the reaction vessel. The second collection vessel provides a second collection chamber 78. The bottom wall 82 of the reaction vessel is a selectively rupturable or frangible bottom. That is, the bottom wall 82 can rupture upon a predetermined pressure being exerted against such bottom wall. The second collection vessel 76 can also contain the label determining reagents for detecting the presence of labeled component. Such label determining reagents can be either in liquid or solid phase.

In operation, a sample suspected of containing a ligand is introduced to the reaction chamber 64. The first collection vessel 68 is then inserted into the reaction vessel to seal the reaction chamber and permit an incubation period for the complex forming reaction to occur. Following the incubation period, the first collection vessel 68 is pushed further into the reaction chamber. Fluid within the reaction mixture and free labeled component flows through the separation medium 74 into the first collection chamber 70. As the first collection vessel approaches the bottom wall 82, substantially all of the liquid and free labeled component flows through the separation medium into the first collection chamber. The bottom wall is formed such that it will withstand the pressure exerted for collecting the filtrate and free labeled component in the first collection chamber.

After the filtrate and free labeled component has been collected, a greater force is exerted on the first collection vessel which is sufficient to translate such force to the bottom wall 82 for rupturing the bottom wall, causing the remaining component of the reaction mixture, which is essentially the formed complex of ligand, binding agent and labeled component, to fall into or transfer to the second collection chamber 78.

The presence of ligand can be determined by determining the presence of labeled component in the filtrate collected in the first collection chamber or determining the presence of labeled component in the complex present in the second collection chamber 78. To facilitate the determination of the labeled component in the complex in the second collection chamber, the labeled component determining reagents 84 present in the second collection chamber begin reacting with the labeled component present in the complex upon rupturing the bottom wall 82. The embodiment shown in FIG. 3 does not require the transfer of the reaction mixture, thus, it aids in inhibiting the transmission of infection.

The method of the present invention comprises contacting, in a liquid medium, a sample containing an unknown amount of ligand and antiligand with predetermined amounts of component or components required to perform a competitive or noncompetitive heterogeneous immunoassay. At least one of the predetermined components is labeled and at least one component is a binding partner to the unknown ligand or antiligand. One or more components can be attached to a macromolecule for enhancing the relative size differential between the resultant formed complex and the free labeled component.

Following formation of antibody-antigen complexes, separation of bound labeled component from free labeled component is performed in a manually operated separation device which effectively separates the larger complex from smaller free component while collecting all liquid test materials in self-contained receptacles which can be a part of the separation device. The particular separation medium can be selected by one having an understanding of the invention herein by distinguishing between the relative sizes of the labeled antibody-antigen complex and free labeled component. Various separation mediums can be used such as membrane filters, depth filters, or gel filtration. The separation step is performed by manipulation of the device to create a pressure differential across the separation medium. The pressure differential produces separation and the liquid filtrate passing through the separation medium is collected in a self-contained enclosure.

The utility of the method herein and the practices illustrated in the following examples are not regarded as limiting.

EXAMPLE 1

Membrane Filtration and Negative Pressure

An experiment was conducted to determine the utility of membrane filtration activated by an evacuated tube containing reagents to measure free component which passes through the filter. In the experiment, an assembly substantially as shown in FIG. 1 was employed. The binding partners consisted of an antigen reagent (ligand) and a labeled antibody reagent (binding partner). The antigen reagent contained fixed and killed *Staphylococcus aureus* cells, commercially available from Seragen. The antigen was prepared such that a 1 to 16 final assay dilution would bind greater than 95% of labeled antibody as could be determined by centrifugation separation.

The labeled antibody reagent was prepared from peroxidase labeled rabbit antimouse IgG (IgG-HRP), commercially available from Sigma. The antimouse IgG was purified on Protein A-Sepharose CL-4B, commercially available from Pharmacia. A 1 to 4,000 final dilution of the reagent resulted in an activity greater than 0.10 increase in adsorbance per minute at 30° Centigrade when mixed with the enzyme substrate (hydrogen peroxide) and color indicator (ABTS).

The assay was conducted by mixing equal parts of the antigen reagent containing *Staphylococcus aureus* cells and the antigen reagent containing IgG-HRP, both of which were diluted in 0.01M phosphate buffered saline (PBS) with 0.25% (by wt.) bovine serum albumin (BSA) and 0.25% Tween 20 (by vol.), commercially available from Sigma. Following mixing of the reagents, the mixture was incubated at room temperature for a sufficient time to bring about complexing of the labeled antibody and antigen. The antibody-antigen complex was separated by filtration using a Cathivex 0.22 millimicron filter, commercially available from Millipore, and attached to a 3 milliliter syringe and a 20 gauge needle. Filtration was performed by creating a pressure differential across the filter by puncturing an evacuated collection tube with the needle. Evacuated collection tubes are commercially available from Becton-Dickinson. Prior to filtration, a small amount of enzyme substrate ($H_2O_2$) and color indicator (ABTS) was added to the collection tube in a manner to maintain sufficient reduced pressure (vacuum) to complete the filtration process. The presence of antigen was determined by monitoring the enzyme activity in the filtrate collected in the collection tube. The presence of antigen was also determined by adding enzyme substrate and color indicator mixture to the antibody-antigen complexes trapped on top of the filter.

EXAMPLE 2

Depth Filter and Positive Pressure

This experiment was conducted to determine the utility of a manually operated, positive pressure, depth filter substantially as shown in FIG. 3. Reagents employed in this assay included *Staphylococcus aureus* antibodies, commercially available from Sigma, which were coupled to CNBr-activated Sepharose 4B, commercially available from Pharmacia, and the same antigen reagent and labeled antibody reagent used in Example 1.

The assay was conducted by mixing the coupled antibody and *Staphylococcus aureus* cells and incubating the mixture at room temperature for sufficient time to bring about complexing of the antigen (Staphylococcus cells) and the sepharose coupled antibody. To the mixture was added labeled antibody, IgG-HRP. This mixture was incubated at room temperature for sufficient time to bring about complexing the IgG-HRP to the coupled antibody-*Staphylyococcus aureus* complexes.

Separation of the labeled macromolecular complexes from free IgG-HRP was performed using a Glasrock 13 mm serum separator with a 5 to 10 millimicron exclusion limit depth filter. At the end of the assay incubation period, the serum separator was inserted into the reaction mixture such that all but the sepharose beads passed through the filter. That is, sepharose bound antibody and antigen complex was excluded while the free labeled antibody passed through the filter. Enzyme activity was readily measured in the filtrate collected in the serum separator using conventional enzyme assay techniques such as set forth in Example 1.

The results obtained in Examples 1 and 2 demonstrate the utility of a heterogeneous immunoassay method wherein bound and free components are separated in a manually operated filtration device which collects and stores the filtrate in a collection chamber. The ability to separate bound and free labeled components is based upon the relative sizes of the two components. When the antibody-antigen complex is significantly larger than the free component, separation can be readily performed.

The ligand determining method and the apparatus herein can be used to determine the presence of a ligand or ligands by providing the appropriate binding partner or binding partners for such ligand or ligands. An advantage herein is that washing steps are not needed nor required in order to determine whether a ligand is present. Such washing steps are required in solid phase assays.

The method herein can be practiced as a competitive heterogeneous assay by providing a labeled component in the suspension, which labeled component is a known concentration of a compound which competes with the ligand for binding sites on the binding partner. The method herein can be practiced as described above as a heterogeneous noncompetitive assay by selecting a labeled component which does not compete with the ligand for binding sites on the binding partner.

The method herein can be used to determine the presence of different ligands in a sample suspected of containing the ligands. In such an assay, the suspension provided in the reaction vessel includes at least one additional labeled component labeled with a different label than any other labeled component present in the suspension and at least one additional binding partner, which additional binding partner is capable of reacting with a different ligand than a first binding partner present in the suspension. In such a suspension, the additional labeled component and additional binding partner can combine with any second ligand to be assayed and suspected of being present in the sample. As will be appreciated, a plurality of assays can be conducted using such a system.

The suspension in the reaction vessel can be provided with a second labeled component to provide a control to the assay for determining the efficiency of the separation medium and thereby the assay. Such a second labeled component can be present in the suspension, which second labeled component is nonreactive to the ligand and binding partner for the ligand. The second labeled component is also labeled with the same label as the first labeled component used for binding to the binding partner, ligand, or reaction product of the binding partner and ligand. The use of such a second labeled component provides a reference control as following separation of the complex from the free first labeled component, the filtrate can be checked to determine the presence of any labeled component in the filtrate. That is, the filtrate is checked to determine the presence of either the first labeled component or the second labeled component. If there is a detectable reaction for the label in the filtrate, then it can be surmised that the separation medium permitted the free first labeled component to pass therethrough. If no label is detected in the filtrate, then it can be surmised that the separation medium did not permit the free labeled component to flow therethrough and thus any detection of the labeled component in the material which did not pass through the separation medium will not provide a determination of the presence of ligand in the sample as it will be masked by the presence of free first labeled component.

We claim:

1. A hand-held assembly for the detection and determination of at least one ligand in a sample suspected of containing such ligand, the assembly comprising:

a vessel having a first chamber for receiving a sample suspected of containing the ligand, which first chamber includes an admixture of a binding partner for such ligand and a labeled component selected from the group consisting of binding partner, compound which can bind to the binding partner, compound which can bind to the reaction product of the ligand and binding partner, and compound which can bind to the ligand;

a second vessel having a second chamber separated from the first chamber by a separation means for permitting the passage therethrough of free labeled component of a relatively small size while preventing the passage therethrough of a complex formed from ligand, binding partner and labeled component of a relatively larger size than the free labeled component, when a pressure differential is created across such separation means;

means for creating a pressure differential across the separation means to separate the free labeled component from the complex and collect the free labeled component in the second chamber; and label detecting reagents in the second chamber.

2. An assembly as recited in claim 1 wherein the admixture of binding partner and labeled component comprises a liquid suspension.

3. An assembly as recited in claim 1 wherein the labeled component comprises a known concentration of a compound which competes with the ligand for binding sites on such binding partner.

4. An assembly as recited in claim 1 wherein the labeled component comprises a known concentration of labeled ligand.

5. An assembly as recited in claim 1 wherein the labeled component comprises labeled binding partner for such ligand.

6. An assembly as recited in claim 1 further comprising a macromolecule in the admixture, which macromolecule comprises a compound capable of binding to a compound selected from the group consisting of ligand, binding partner and complex of ligand and binding partner.

7. An assembly as recited in claim 1 further comprising a second labeled component in the admixture, which second labeled component is non-reactive and labeled with the same label as the first labeled component.

8. An assembly as recited in claim 1 further comprising at least one additional labeled component in the admixture, which is labeled with a different label than any other labeled component present in the admixture in the first chamber; and at least one additional binding binding partner in such admixture, which such additional binding partner is capable of reacting with a different ligand which can be present in the sample.

9. An assembly as recited in claim 1 wherein the first vessel comprises:

a generally cylindrical vessel defining the first chamber and the separation means is positioned within the first chamber;

an outlet port on the first vessel in fluid flow communication with the first chamber through such separation means;

a needle hub means attached to the outlet port for retaining a needle cannula on the outlet port;

a needle cannula attached to the needle hub means; and such second vessel comprises a generally cylindrically vessel defining a second chamber with a reduced pressure therein and a puncturable cover sealing the second chamber.

10. An assembly as recited in claim 9 further comprising a projecting wall portion on the first vessel, which projecting wall portion extends around the needle hub means and needle cannula and defines a cavity therewithin for receiving the second vessel.

11. An assembly as recited in claim 1 wherein the first vessel comprises:
a generally cylindrical vessel defining the first chamber therewithin and the second vessel comprises a generally cylindrical vessel removably positioned within the first chamber of the first vessel and wherein the separation means is positioned within the second vessel; and
further comprising sealing means on the second vessel for providing a liquid seal between the second vessel and first vessel for preventing liquid from flowing into the annulus created between the first and second vessels.

12. An assembly as recited in claim 11 further comprising:
a frangible bottom wall of the first chamber of the first vessel, which frangible bottom wall is selectively frangible upon a preselected pressure being exerted against such frangible bottom wall; and
a third vessel attached to the first vessel, which third vessel defines a third chamber in communication with the first chamber upon fracturing the frangible bottom wall of the first vessel.

13. An assembly as recited in claim 12 further comprising label detecting reagents in the third chamber of the third vessel.

14. A kit for the detection and determination of at least one ligand in a sample suspected of containing such ligand, the kit comprising:
a first vessel having a first chamber for receiving a sample suspected of containing the ligand, which first chamber includes an admixture of a binding partner for such ligand and a labeled component selected from the group consisting of binding partner, compound which can bind to the binding partner, compound which can bind to the reaction product of the ligand and binding partner, and compound which can bind to the ligand;
a separation means provided in the first vessel for permitting the passage therethrough of free labeled component of a relatively small size while preventing the passage therethrough of a complex formed from ligand, binding partner and labeled component of a relatively larger size than the free labeled component when a pressure differential is created across such separation means;
a second vessel having a second chamber having a reduced pressure therein;
label detecting reagent in the second chamber of the second vessel; a puncturable top enclosing the second chamber of the second vessel; an outlet port on the first vessel;
a needle hub attached to the outlet port of the first vessel; and a needle cannula attached to the needle hub, which needle cannula is capable of piercing the top on the second vessel to expose the separation medium to the reduced pressure in the second vessel and create a pressure differential across the separation means for separating the free labeled component from the complex, which free labeled component flows through the needle cannula and is collected in the second chamber of the second vessel.

15. A kit as recited in claim 14 further comprising a third vessel having a third chamber therein with a reduced pressure in the third chamber; a puncturable top on the third vessel sealing the third chamber, which puncturable top is puncturable by the needle cannula on the first vessel.

16. A kit as recited in claim 37 further comprising a label detecting reagent present in the third chamber of the third vessel.

17. A kit as recited in claim 14 further comprising a liquid suspending agent for introducing to the first chamber in the first vessel to provide a liquid suspension of the binding partner and labeled component.

18. A kit as recited in claim 14 wherein the admixture in the first chamber of the first vessel comprises a liquid suspension of binding partner and labeled component.

19. A kit for the detection and determination of at least one ligand in a sample suspected of containing such ligand, the kit comprising:
a first vessel having a first chamber for receiving a sample suspected of containing ligand, which first chamber includes an admixture of a binding partner for such ligand and a label component selected from the group consisting of binding partner, compound which can bind to the binding partner, compound which can bind to the reaction product of the ligand and binding partner, and compound which can bind to the ligand;
a second vessel having a second chamber capable of being positioned within the first chamber of the first vessel, which second vessel includes sealing means for sealing the annulus between the second and first vessel to fluid flow;
separation means in the second chamber for permitting the passage therethrough of free labeled component of a relatively small size while preventing the passage therethrough of a complex formed from ligand, binding partner, and label component of a relatively larger size than the free labeled component when a pressure differential is created across such separation means; and
label detecting reagent in the second chamber of the second vessel.

20. A kit as recited in claim 19 wherein the admixture comprises a liquid suspension of the binding partner and labeled component.

21. A kit as recited in claim 19 further comprising a liquid suspending agent for introducing to the first chamber of the first vessel to provide a liquid suspension of the binding partner and labeled component.

22. A kit as recited in claim 19 further comprising a third vessel attachable to the first vessel and separated from the first vessel by a frangible bottom wall on the first vessel.

23. A kit as recited in claim 22 further comprising label detecting reagent present in the third chamber of the third vessel.

* * * * *

UNITED STATES PATENT AND TRADEMARK OFFICE
CERTIFICATE OF CORRECTION

PATENT NO. : 4,786,471
DATED : November 22, 1988
INVENTOR(S) : Linda L. Jones and Edward T. Maggio It is certified that error appears in the above-identified patent and that said Letters Patent are hereby corrected as shown below:

In column 1, line 29, delete "doe" and insert --do--.

In column 1, line 37, delete "an" and insert --as--.

In column 4, line 34, delete "solvent" and insert --solvents--.

In column 5, line 55, delete "forces" and insert --forced--.

In column 9, line 61, delete "adsorbance" and insert --absorbance--.

Signed and Sealed this

Twenty-fifth Day of April, 1989

Attest:

DONALD J. QUIGG

*Attesting Officer*       *Commissioner of Patents and Trademarks*